(12) United States Patent
Hammett et al.

(10) Patent No.: US 11,857,144 B2
(45) Date of Patent: Jan. 2, 2024

(54) LONGITUDINAL-POSITIONING INDICATOR AND MARKING GRID

(71) Applicants: Bradley Hammett, Sherman, TX (US); Stephanie Hammett, Sherman, TX (US)

(72) Inventors: Bradley Hammett, Sherman, TX (US); Stephanie Hammett, Sherman, TX (US)

(*) Notice: Subject to any disclaimer, the term of this patent is extended or adjusted under 35 U.S.C. 154(b) by 0 days.

(21) Appl. No.: 18/126,660

(22) Filed: Mar. 27, 2023

(65) Prior Publication Data

US 2023/0225682 A1 Jul. 20, 2023

Related U.S. Application Data

(63) Continuation of application No. 17/142,645, filed on Jan. 6, 2021, now Pat. No. 11,612,364.

(51) Int. Cl.
*A61B 6/04* (2006.01)
*A61B 90/00* (2016.01)

(52) U.S. Cl.
CPC ............ *A61B 6/0492* (2013.01); *A61B 90/39* (2016.02); *A61B 2090/3966* (2016.02)

(58) Field of Classification Search
CPC .............. A61B 6/0492; A61B 90/39; A61B 2090/3966
See application file for complete search history.

(56) References Cited

U.S. PATENT DOCUMENTS

| | | | |
|---|---|---|---|
| 5,052,035 A * | 9/1991 | Krupnick | A61B 6/08 378/162 |
| 6,333,970 B1 | 12/2001 | Lemaitre et al. | |
| 6,714,628 B2 | 3/2004 | Broyles et al. | |
| 6,928,146 B2 | 8/2005 | Broyles et al. | |
| 8,012,295 B1 | 9/2011 | Broyles | |
| 2003/0081732 A1* | 5/2003 | Broyles | A61B 6/12 378/162 |
| 2004/0076261 A1 | 4/2004 | Broyles et al. | |
| 2004/0103903 A1 | 6/2004 | Falahee | |
| 2005/0004581 A1 | 1/2005 | Astrom | |
| 2007/0269016 A1 | 11/2007 | Mackey | |
| 2009/0177077 A1 | 7/2009 | Piferi et al. | |
| 2013/0150703 A1 | 6/2013 | Buchalter et al. | |
| 2014/0094678 A1 | 4/2014 | Traboulsi et al. | |
| 2014/0221819 A1 | 8/2014 | Sarment | |
| 2016/0123903 A1 | 5/2016 | Barrett et al. | |

FOREIGN PATENT DOCUMENTS

| | | |
|---|---|---|
| JP | 2013518630 A | 5/2013 |
| WO | 2014032171 A1 | 3/2014 |
| WO | 2014127354 A1 | 8/2014 |

* cited by examiner

*Primary Examiner* — Mark R Gaworecki
(74) *Attorney, Agent, or Firm* — Stephen Y. Liu; Carstens, Allen & Gourley, LLP

(57) ABSTRACT

A longitudinal-positioning indicator, improved marking grid, and a method of use. The longitudinal-positioning indicator includes a substrate that has a first side on which a set of longitudinal-positioning guidelines are disposed, the set of longitudinal-positioning guidelines configured to indicate a position along a length of the longitudinal-positioning guidelines based on a cross-section of the longitudinal-positioning indicator taken substantially orthogonally to the set of longitudinal-positioning guidelines. The substrate also has a second side that is at least partially coated with an adhesive.

19 Claims, 14 Drawing Sheets

LONGITUDINAL-POSITIONING INDICATOR AND MARKING GRID

STATEMENT OF RELATED APPLICATIONS

This application is a continuation of pending U.S. Ser. No. 17/142,645, filed on Jan. 6, 2021, of which is incorporated herein by reference in its entirety.

BACKGROUND

Technical Field

Novel aspects of the present disclosure relate to a guide for providing reference indicators for use in radiographic imaging. More particularly, the present disclosure is directed to a longitudinal-positioning indicator and an improved marking grid for use in radiographic imaging, which can provide orthogonal coordinates for identifying locations on a patient's body for performing medical procedures.

Background

Computerized tomography (CT) scanning is a radiographic imaging procedure that creates cross-sectional images in the transverse plane, colloquially described as "slices", to depict target internal structures (e.g., organs or tumors) of a patient within the scanned areas. Appearance of objects depicted on a CT image is based in part on radiotransparency. Denser substances, such as bones and rigid implants are substantially radiopaque and appear on a radiographic image as white. Body cavities are radiolucent and appear as dark regions. Soft tissue is generally more radiopaque than body cavities and appear in various shades of gray based on density.

A CT scanning system generally includes a scanner, a bed configured to advance a patient through the scanner, and a computer that constructs the image slices based on the image data captured by the scanner. To provide some context that can be used identify the location of the target internal structures, marking grids with substantially radiopaque guidelines can be adhered to a patient so that the marking grids appear on the radiographic image. However, conventionally available marking grids only include lateral-positioning guidelines for identifying, from a radiographic image, a lateral position for location determination. The patient's table position is used to provide a second, longitudinal position for location determination. However, translation or rotation of the patient's body relative to the scanning table can render the longitudinal position inaccurate.

SUMMARY OF THE INVENTION

Novel aspects of the disclosure are directed to a longitudinal-positioning indicator for use in radiographic imaging procedures, an improved marking grid including the longitudinal-positioning indicator, and a method of use. The longitudinal-positioning indicator includes a substrate that has a first side on which a set of longitudinal-positioning guidelines are disposed, the set of longitudinal-positioning guidelines configured to indicate a position along a length of the longitudinal-positioning guidelines based on a cross-section of the longitudinal-positioning indicator taken substantially orthogonally to the set of longitudinal-positioning guidelines. The substrate also has a second side that is at least partially coated with an adhesive.

The improved marking grid includes a substrate including a first side and a second side that is at least partially coated with an adhesive. The marking grid also includes a set of lateral-positioning guidelines supported by the substrate and a set of longitudinal-positioning guidelines supported by the substrate. The set of lateral-positioning guidelines and the set of longitudinal-positioning guidelines are configured to provide a pair of orthogonal coordinates that indicate a location within an area bounded by the marking grid, the location based on a cross-section of the marking grid taken substantially orthogonally to the set of lateral-positioning guidelines.

The method is directed to needle insertion into a patient within an area defined by a marking grid, the marking grid including a set of lateral-positioning guidelines and a set of longitudinal-positioning guidelines configured to provide reference markers based on a cross-section of the marking grid taken substantially orthogonally to the set of lateral-positioning guidelines, the method including the steps of identifying, from a radiographic image, a target internal structure; identifying, from reference markers associated with the set of lateral-positioning guidelines, a lateral-positioning coordinate for the target internal structure; identifying, from reference markers associated with the set of longitudinal-positioning guidelines, a longitudinal-positioning coordinate for the target internal structure; and determining, with reference to indicators on the marking grid, a location for the needle insertion using the longitudinal-positioning coordinate and the lateral-positioning coordinate.

Other aspects, embodiments and features of the invention will become apparent from the following detailed description of the invention when considered in conjunction with the accompanying figures. In the figures, each identical, or substantially similar component that is illustrated in various figures is represented by a single numeral or notation. For purposes of clarity, not every component is labeled in every figure. Nor is every component of each embodiment of the invention shown where illustration is not necessary to allow those of ordinary skill in the art to understand the invention.

BRIEF DESCRIPTION OF THE FIGURES

The novel features believed characteristic of the invention are set forth in the appended claims. The invention itself, however, as well as a preferred mode of use, further objectives, and advantages thereof, will be best understood by reference to the following detailed description of illustrative embodiments when read in conjunction with the accompanying figures, wherein:

DETAILED DESCRIPTION

Figure 1A:
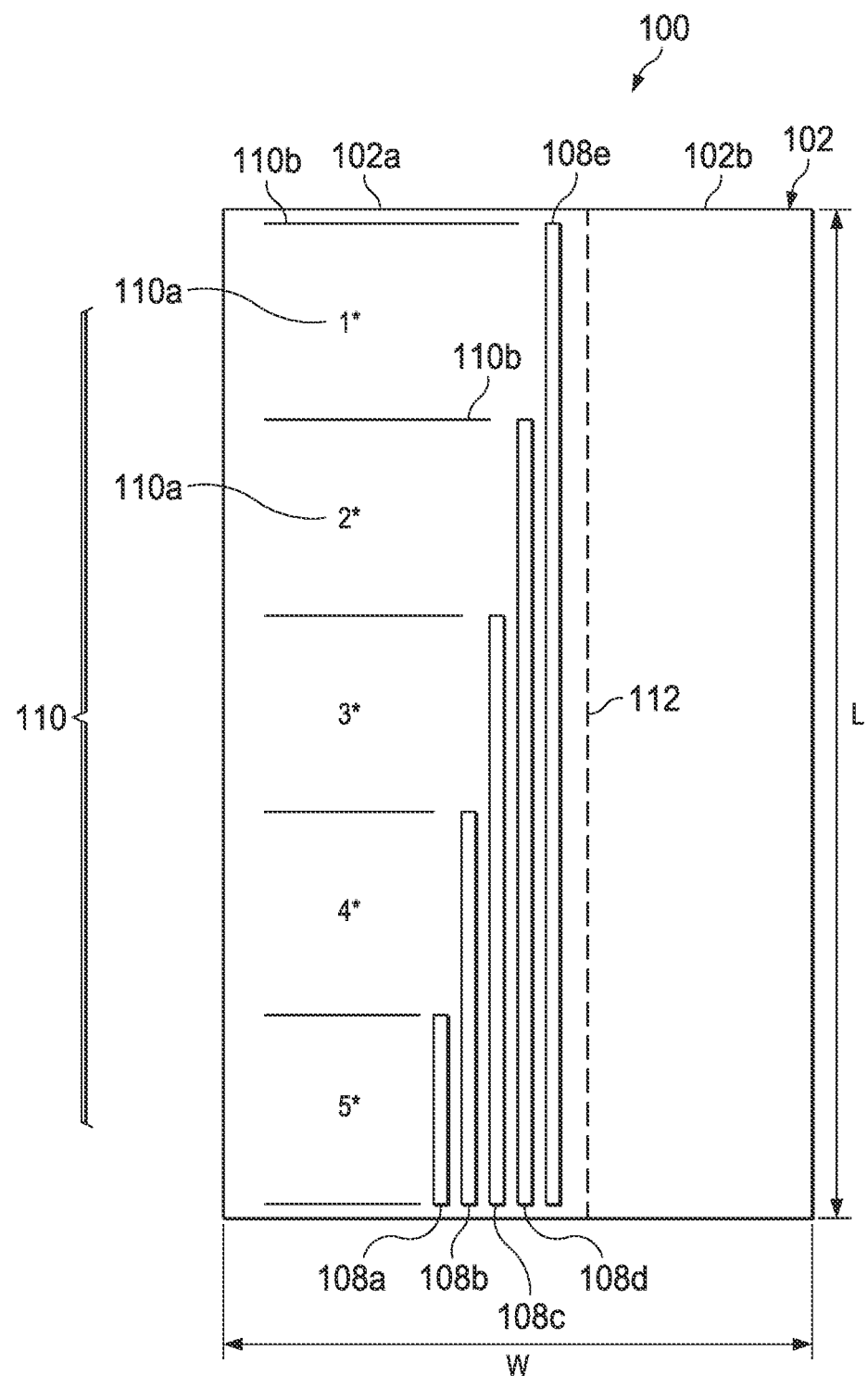
FIGS. 1A and 1B are drawings depicting a plan view and a perspective view of a longitudinal-positioning indicator, respectively, in accordance with an illustrative embodiment.

Marking grids are commonly used during radiographic imaging procedures, such as a CT-guided biopsy procedure, to provide a radiologist or technician, also referred to herein as a "user", with reference markers for biopsy needle insertion. Conventional marking grids, such as marking grid 300 depicted in FIG. 3, generally include a plurality of lateral-positioning guidelines, i.e. a series of elongated, parallel, and coextensive guidelines that are regularly spaced apart and formed from a radiopaque substance so that the guidelines appear clearly in a radiographic image. Neighboring guidelines may be separated from one another by an elongated aperture. The marking grid can be applied to a recipient, also referred to herein as "a patient," so that when the recipient is in a supine position, the elongated guidelines are aligned substantially orthogonally to the transverse plane and positioned over an area of interest containing an internal structure to be scanned.

When a CT scan is performed of the area of interest, a predetermined number of sequential CT images are captured, which depict the transverse slices of the internal structure along with the guidelines from the marking grid. The guidelines appear in cross-section on each of the CT images as solid white circles. Needle insertion into the scanned internal structure can be achieved by determining, from a selected CT image, depth and lateral positioning (i.e., a lateral-positioning coordinate) based on the reference markers, and longitudinal positioning (i.e., a longitudinal-positioning coordinate) based on the patient's table position. Thereafter, the location for needle insertion can be identified on a user's skin with reference to the lateral-positioning guidelines on the marking grid, which establishes the lateral-positioning coordinate, and a patient's table position, which establishes the longitudinal-positioning coordinate.

Inadvertent translation and/or rotation of the patient on the scanning table can result in inaccurate location determination. Thus, novel aspects of this disclosure recognize a need for providing a reference marker that can indicate a longitudinal position in a radiographic image so that a single radiographic image can be used to determine a lateral-positioning coordinate, longitudinal-positioning coordinate, and a depth for biopsy needle insertion. The lateral and longitudinal-positioning coordinates are provided by indicators that can convey the positioning information from a cross-section of the indicators, taken in the transverse plane so that the positioning information can be determined from a radiographic image.

In the disclosure that follows, FIGS. 1-7 are directed to a longitudinal-positioning indicator that can be applied to existing marking grids that are only capable of providing a lateral-positioning coordinate. FIGS. 8-14 are directed to an improved marking grid that includes lateral-positioning guidelines and longitudinal-positioning guidelines that are capable of providing both a lateral-positioning coordinate and a longitudinal-positioning coordinate.

Figure 1B:
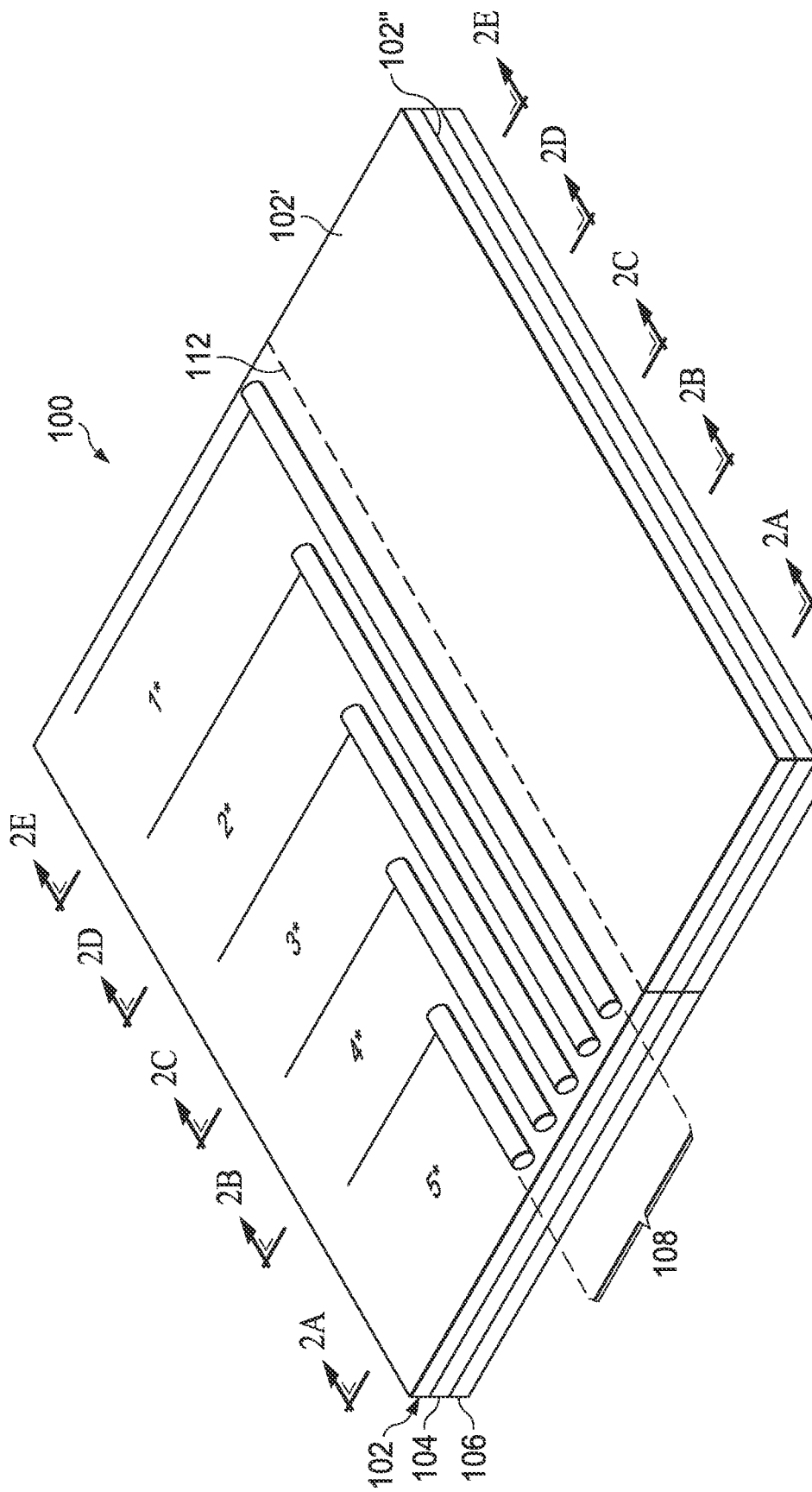
Figure 2A:
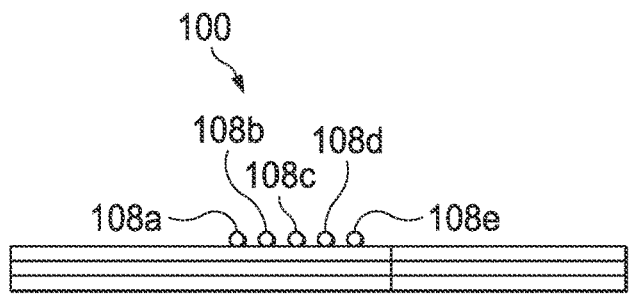
FIGS. 2A-2E are drawings depicting cross-sectional views of the longitudinal-positioning indicator taken along lines 2a-2a, 2b-2b, 2c-2c, 2d-2d, and 2e-2e, respectively, in FIG. 1B.
Figure 2B:
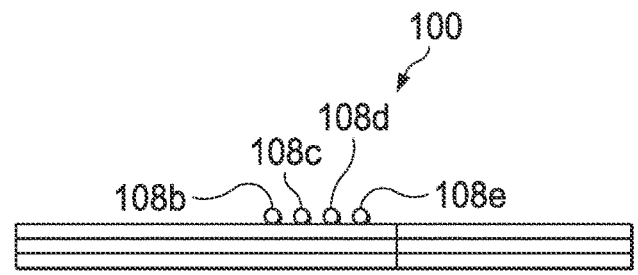
Figure 2C:
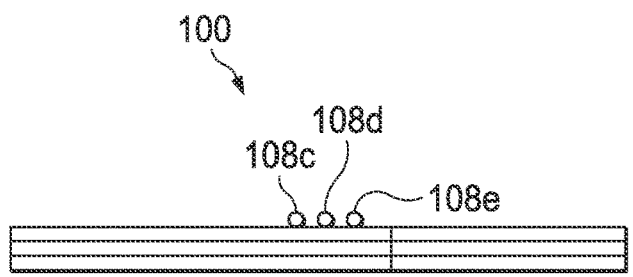
Figure 2D:
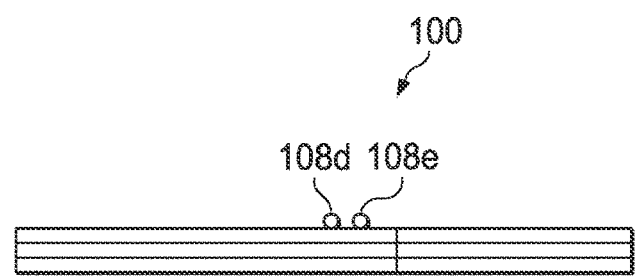
Figure 2E:
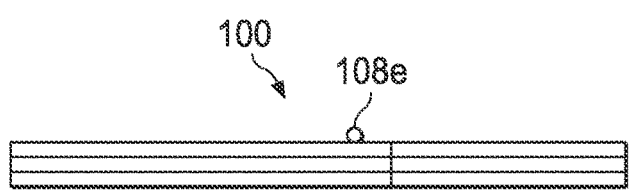

FIGS. 1A and 1B are drawings depicting a plan view and a perspective view, respectively, of a longitudinal-positioning indicator in accordance with an illustrative embodiment. The longitudinal-positioning indicator 100 has a length L that extends in the longitudinal direction and a width W that extends in a lateral direction that is substantially orthogonal to the longitudinal direction. As used herein, the lateral direction may also be referred to in the alternative as the transverse direction. The longitudinal-positioning indicator 100 is configured to indicate a relative position along the length L of the longitudinal-positioning indicator 100 from a cross-section taken in a transverse plane. Thus, the longitudinal-positioning indicator 100 can be used to indicate a relative position along the length L of the longitudinal-positioning indicator 100 from a radiographic image, as described in more detail in the discussion of the various embodiments that follow.

The longitudinal-positioning indicator 100 includes a substrate 102 that is generally radiolucent. The substrate 102 is flexible and can be elastic in some embodiments to conform to the contours of a patient's body. Non-limiting examples of materials for forming the substrate 102 can include paper, plastic, or fabric. The substrate 102 has a first side 102' and a second side 102" opposite to the first side 102'. An adhesive 104 is applied to at least a portion of the second side 102" to enable the longitudinal-positioning indicator 100 to be affixed to target location, such as a marking grid or to a patient's skin. Prior to use, the longitudinal-positioning indicator 100 can be releasably adhered to a releasable backing material 106 via the adhesive 104.

In this illustrative embodiment in FIG. 1, a set of longitudinal-positioning guidelines 108 is disposed on the first side 102' of the longitudinal-positioning indicator 100. As used herein, the term "set" means one or more. Thus, the set of longitudinal-positioning guidelines 108 can be a single guideline or two or more longitudinal-positioning guidelines. With particular reference to FIGS. 1A and 1B, the set of longitudinal-positioning guidelines 108 includes five guidelines 108a-108e aligned at their respective first ends and extend in a longitudinal direction. As used herein, the "longitudinal direction" corresponds to the length L of the longitudinal-positioning indicator 100 so that so that a cross-sectional view of the longitudinal-positioning indicator 100 is orthogonal to each of the guidelines in the set of longitudinal-positioning guidelines 108.

Figure 5:
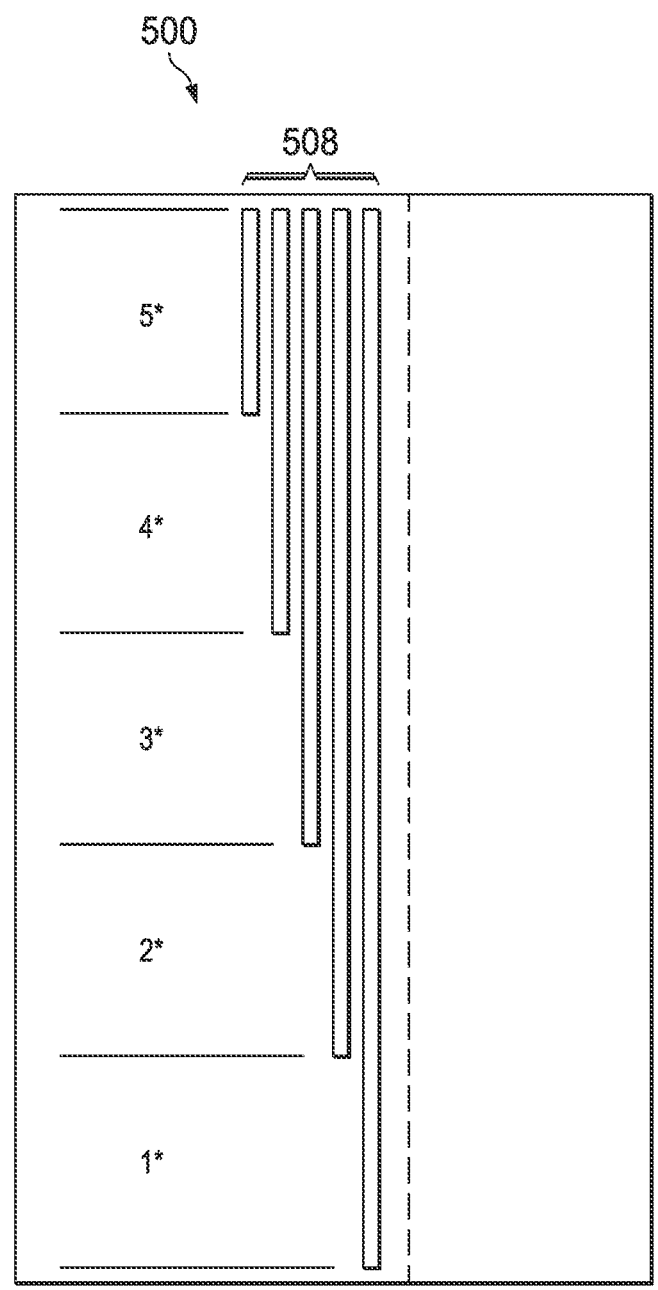
FIG. 5 is a drawing depicting a plan view of a longitudinal-positioning indicator in accordance with another illustrative embodiment.

Each of the guidelines in the set of longitudinal-positioning guidelines 108 has a different length, arranged based on their respective lengths. For example, in the embodiment depicted in FIG. 1 the set of longitudinal-positioning guidelines 108 are arranged in order of increasing length from left to right, i.e., in a stairstep pattern. In another embodiment, as depicted in FIG. 5, the set of longitudinal-positioning guidelines 508 are aligned at their respective second ends and are arranged in order of increasing length from left to right, i.e., in an inverted stairstep pattern.

The set of longitudinal-positioning guidelines 108 can be formed from a substance that is at least partially radiopaque, or in some embodiments substantially entirely radiopaque. In another embodiment, the set of longitudinal-positioning guidelines 108 is formed from substance that has a radiopacity that is greater than the radiopacity of the substrate 102 so that the structure associated with the substrate 102 can be differentiated from the structures associated with the set of longitudinal-positioning guidelines 108 in a radiographic image. For example, the set of elongated indicators can be formed from metal wire or printed onto the substrate 102 using an ink that is at least partially radiopaque. In another embodiment, the set of elongated indicators can be radiopaque particles suspended in a carrier, such as glue, which can be applied to the first side 102' of the substrate 102. In other embodiments, rather than being disposed on the first side 102' of the substrate, the longitudinal-positioning guidelines 108 can be wholly or partially embedded within the substrate 102.

In this illustrative embodiment in FIG. 1, the longitudinal-positioning indicator 100 includes an index 110 including values 110a and/or demarcations 110b, each of which corresponds to a length of a guideline in the set of longitudinal-positioning guidelines 108. For example, each of the values 110a and/or demarcations 110b in the index 110 allows a user to identify a particular guideline in the set of longitudinal-positioning guidelines 108 quickly and easily. By extrapolating each of the demarcations in a transverse direction, an imaginary horizontal axis can be derived. Thus, when the longitudinal-positioning indicator 100 is applied to a conventional marking grid, such as marking grid 300 in FIG. 3 or marking grid 400 in FIG. 4, subsequently captured radiographic image will include reference markers for determining a longitudinal-positioning coordinate that can be correlated to a location on a patient's skin with reference to the index 110.

Figure 3:
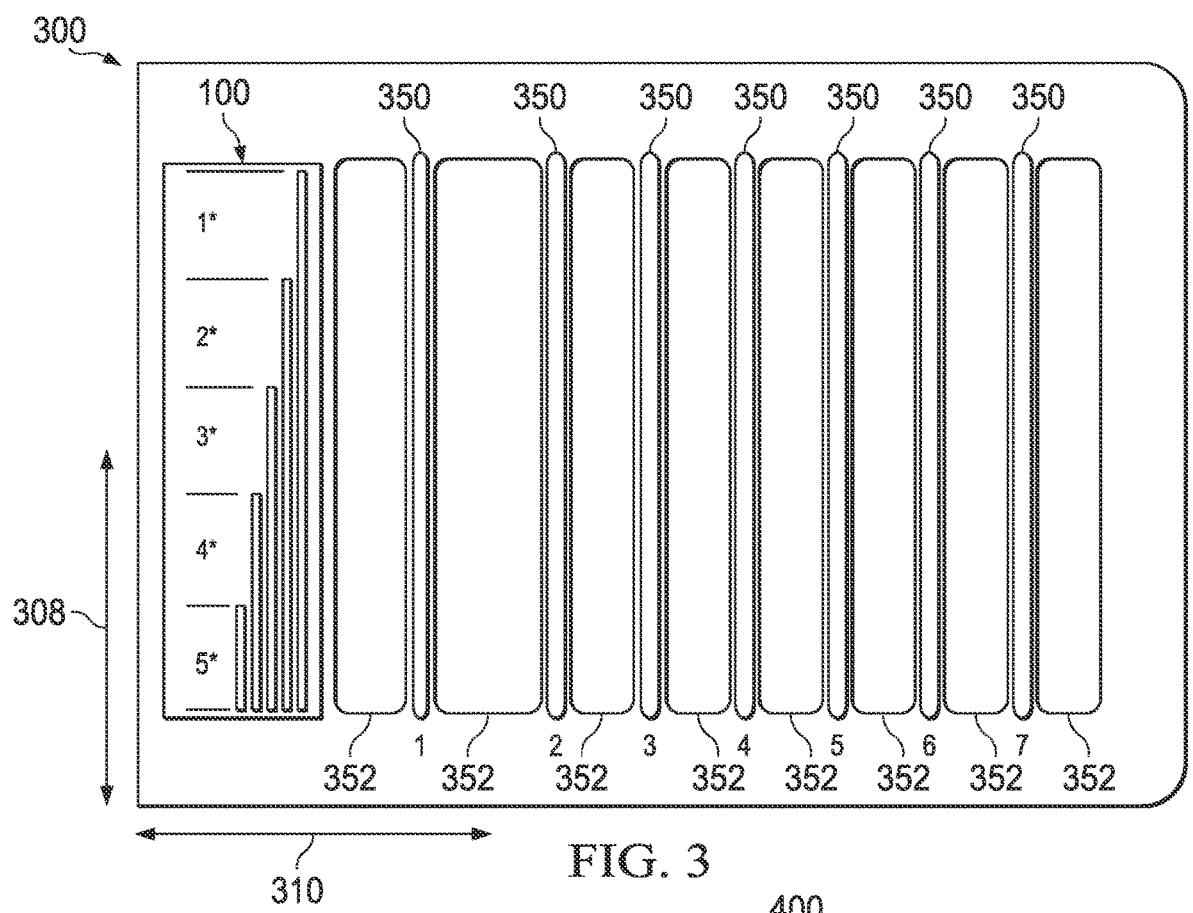
FIG. 3 is a drawing depicting a plan view of a longitudinal-positioning indicator applied to a marking grid according to an illustrative embodiment.
Figure 4:
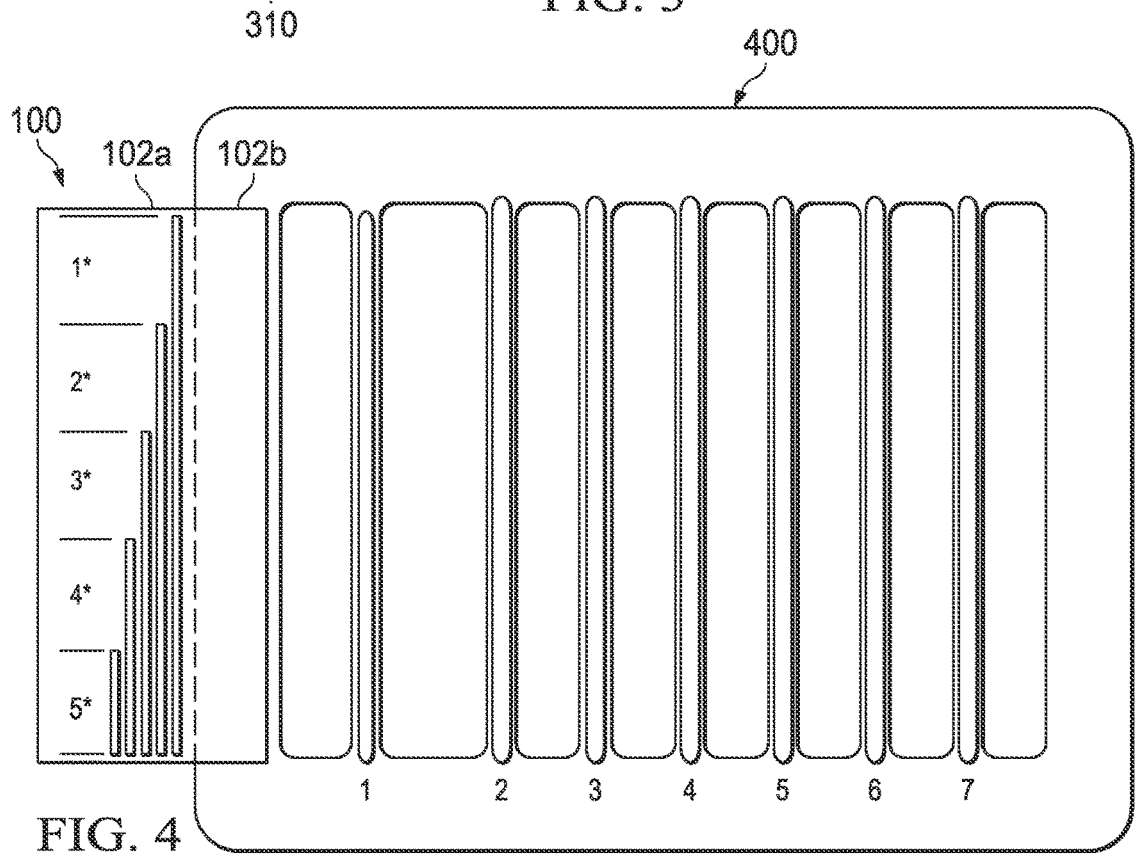
FIG. 4 is a drawing depicting a plan view of a longitudinal-positioning indicator applied to a marking grid according to another illustrative embodiment.

In this illustrative embodiment in FIG. 1, the substrate 102 of longitudinal-positioning indicator 100 includes a body portion 102a that supports the set of longitudinal-positioning guidelines 108 and an optional margin portion 102b. In some embodiments, the body portion 102a can be separated from the margin portion 102b by a perforation 112 that allows the body portion 102a to be detached from the margin portion 102b. The perforation 112 permits the body portion 102a to be separated from the margin portion 102b so that the longitudinal-positioning indicator 100 can be at least partially adhered to conventional marking grids, as depicted in FIGS. 3 and 4, or alongside conventional marking grids to permit identification in a longitudinal direction.

In some embodiments, the perforation 112 extends through the substrate 102, the adhesive 104, and the releasable backing material 106. In other embodiments, the perforation 112 extends only through the releasable backing material 106 so that the adhesive 104 is selectively exposed from either the body portion 102a or the margin portion 102b for ease of application.

FIGS. 2A-2E are drawings depicting cross-sectional views of the longitudinal-positioning indicator taken along lines 2a-2a, 2b-2b, 2c-2c, 2d-2d, and 2e-2e, respectively, in FIG. 1B.

As briefly discussed above, the set of longitudinal-positioning guidelines 108 can be used to indicate a longitudinal-positioning coordinate, i.e., a position along a length L of the longitudinal-positioning indicator 100 from a cross-section of the longitudinal-positioning indicator 100. For example, a cross-section of the longitudinal-positioning indicator 100 taken along line 2A-2A will depict five of the set of longitudinal-positioning guidelines 108, e.g., 108a-108e. A cross-section of the longitudinal-positioning indicator 100 taken along lines 2B-2B will depict only four of the set of longitudinal-positioning guidelines 108, e.g., 108b-108e. A cross-section of the longitudinal-positioning indicator 100 taken along lines 2C-2C will depict only three of the set of longitudinal-positioning guidelines 108, e.g., 108c-108e. A cross-section of the longitudinal-positioning indicator 100 taken along lines 2D-2D will depict only two of the set of longitudinal-positioning guidelines 108, e.g., 108d and 108e. A cross-section of the longitudinal-positioning indicator 100 taken along lines 2E-2E will depict only one of the set of longitudinal-positioning guidelines 108, e.g., 108e. Thus, from a cross-section of the longitudinal-positioning indicator 100, a relative position can be determined along a length L.

Because the set of longitudinal-positioning guidelines 108 are at least partially radiopaque, the set of longitudinal-positioning guidelines 108 can serve as reference markers on a radiographic image. When used in conjunction with a marking grid that only includes a set of lateral-positioning guidelines, i.e., only provides a lateral-positioning coordinate, the longitudinal-positioning indicator 100 can provide a longitudinal-positioning coordinate for identifying a location for biopsy needle placement without the need for referring to a patient's table position.

The longitudinal-positioning indicator 100 can be at least partially adhered to conventionally available marking grids. For example, the longitudinal-positioning indicator 100 can be adhered entirely to a conventional marking grid, as depicted in FIG. 3, or the partially adhered to the conventional marking grid as depicted in FIG. 4. Although not depicted, the longitudinal-positioning indicator 100 can be aligned with a conventional marking grid but adhered entirely to a patient's skin.

FIG. 3 is a drawing depicting a plan view of a longitudinal-positioning indicator applied to a marking grid according to an illustrative embodiment. The marking grid 300 is an example of a conventionally available marking grid, which includes a substrate 302 on which a plurality of lateral-positioning guidelines 350 are disposed. Each of the lateral-positioning guidelines 350 are formed from a generally radiopaque substance and are configured to provide reference markers in a radiographic image. The marking grid 300 also includes a plurality of elongated apertures 352 extending substantially co-extensively with each of the plurality of lateral-positioning guidelines 350. The marking grid 300 can be used to determine a lateral-positioning coordinate in a manner that is known in the art. When used in conjunction with the marking grid 300, the longitudinal-positioning indicator 100 provides a longitudinal-positioning coordinate in the manner that was described in detail with reference to FIG. 2.

In this illustrative embodiment in FIG. 3, only the body portion 102a of the longitudinal-positioning indicator 100 is used. In particular, the body portion 102a is adhered directly to the marking grid 300. If the longitudinal-positioning indicator 100 includes the optional margin portion 102b, then the margin portion 102b can be detached from the body portion 102a so that the body portion 102a can be adhered to the marking grid 300. In one embodiment, the margin portion 102b is detached from the body portion 102a along a perforation, such as perforation 112 that was described in more detail in FIG. 1, above. In another embodiment, the longitudinal-positioning indicator 100 can be adhered directly to a patient's skin, positioned adjacent to the marking grid 300 with the set of longitudinal-positioning guidelines 108 oriented substantially parallel to the set of lateral-positioning guidelines 306. In yet another embodiment, the longitudinal-positioning indicator 100 can be partially adhered to the marking grid 300, as described in the figure that follows.

FIG. 4 is a drawing depicting a plan view of a longitudinal-positioning indicator applied to a marking grid according to another illustrative embodiment. The marking grid 400 is an example of a conventionally available marking grid, like marking grid 300 in FIG. 3. The marking grid 300 can be used to determine a lateral-positioning coordinate in a manner that is known in the art. When used in conjunction with the marking grid 400, the longitudinal-positioning indicator 100 provides a longitudinal-positioning coordinate in the manner that was described in detail with reference to FIG. 2.

In this illustrative embodiment in FIG. 4, only the margin portion 102b of the longitudinal-positioning indicator 100 is adhered to the marking grid 400. The body portion 102a extends past the edge of the marking grid 400 and can be adhered directly to a patient's skin. However, in another embodiment the entirety of the longitudinal-positioning indicator 100 in FIG. 4 can be adhered to the marking grid 400 if space permits, or the entirety of the longitudinal-positioning indicator 100 can be adhered to a patient's skin and positioned adjacent to the marking grid 400 with the set of longitudinal-positioning guidelines 108 aligned substantially parallel to the lateral-positioning guidelines.

At least one benefit of applying the longitudinal-positioning indicator 100 depicted in FIG. 4 is the ability to easily align the longitudinal-positioning indicator 100 with the marking grid 400. For example, one side of the longitudinal-positioning indicator can be aligned with the marking grid 400, e.g., the margin portion 102b can be aligned with the edge of the marking grid 400, while the releasable backing material 106 is removed from the other side of the longitudinal-positioning indicator 100 and adhered to a patient's skin or the marking grid 400. Thereafter, the releasable backing material 106 can be removed from the one side of the longitudinal-positioning indicator 100 and adhered.

FIG. 5 is a drawing depicting a plan view of a longitudinal-positioning indicator in accordance with another illustrative embodiment. The longitudinal-positioning indicator 500 is similar to the longitudinal-positioning indicator 100 depicted in FIG. 1, except that each of longitudinal-positioning guidelines 508 are aligned at their respective second ends and arranged in order of increasing size from left to right, forming an inverted stair-step pattern.

Figure 6:
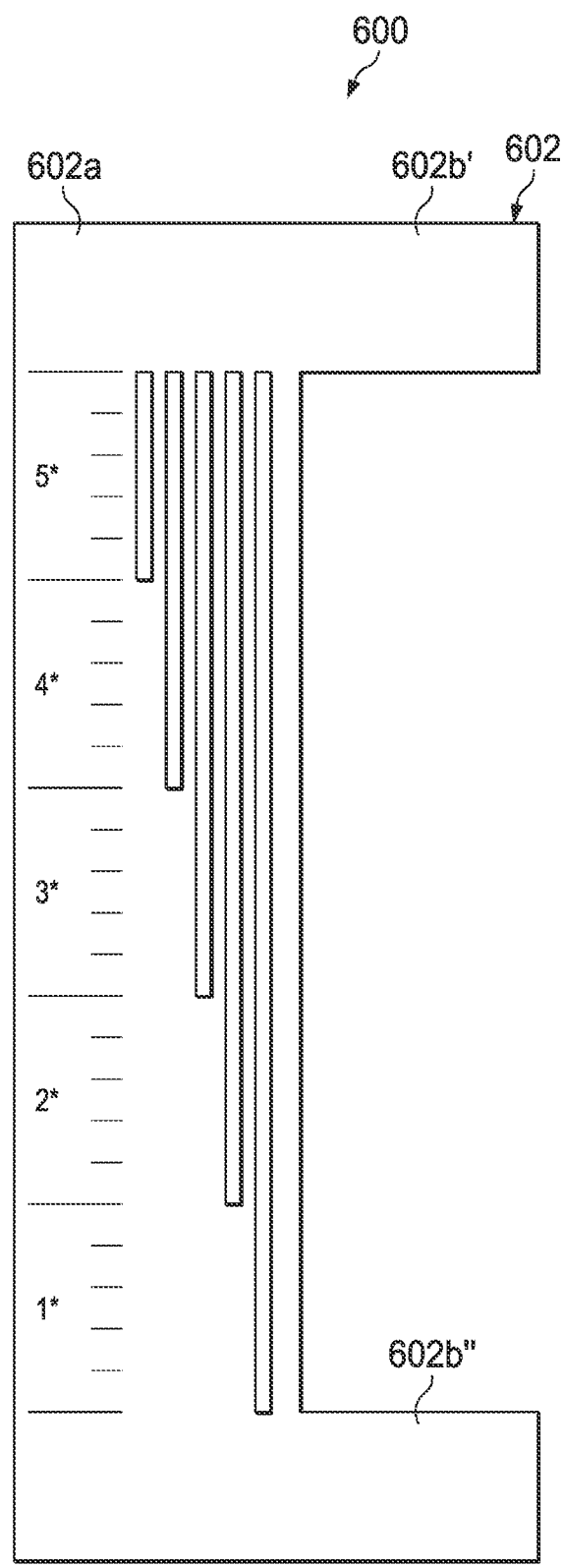
FIG. 6 is a drawing depicting a plan view of a longitudinal-positioning indicator in accordance with yet another illustrative embodiment.

FIG. 6 is a drawing depicting a plan view of a longitudinal-positioning indicator in accordance with yet another illustrative embodiment. The longitudinal-positioning indicator is similar to the longitudinal-positioning indicator in FIG. 5 but includes a margin portion 602b extending outwardly from the body portion 602a. The margin portion 602b is formed from a set of tabs 602b' and 602b". In this illustrative embodiment, each of the tabs 602b' and 602b" are integrally formed with the body portion 602a of the substrate 602. However, in another embodiment, the set of tabs 602b' and 602b" are removably attached to the body portion 602a, e.g., via a perforated edge. In either embodiment, each of the tabs 602b may be releasably adhered to a releasable backing material that is detachable from the releasable backing material adhered to the back of the body portion 602a to allow the releasable backing material of the set of tabs 602b' and/or 602b" to be selectively exposed independently from the releasable backing material adhered to the body portion 602a.

Figure 7:
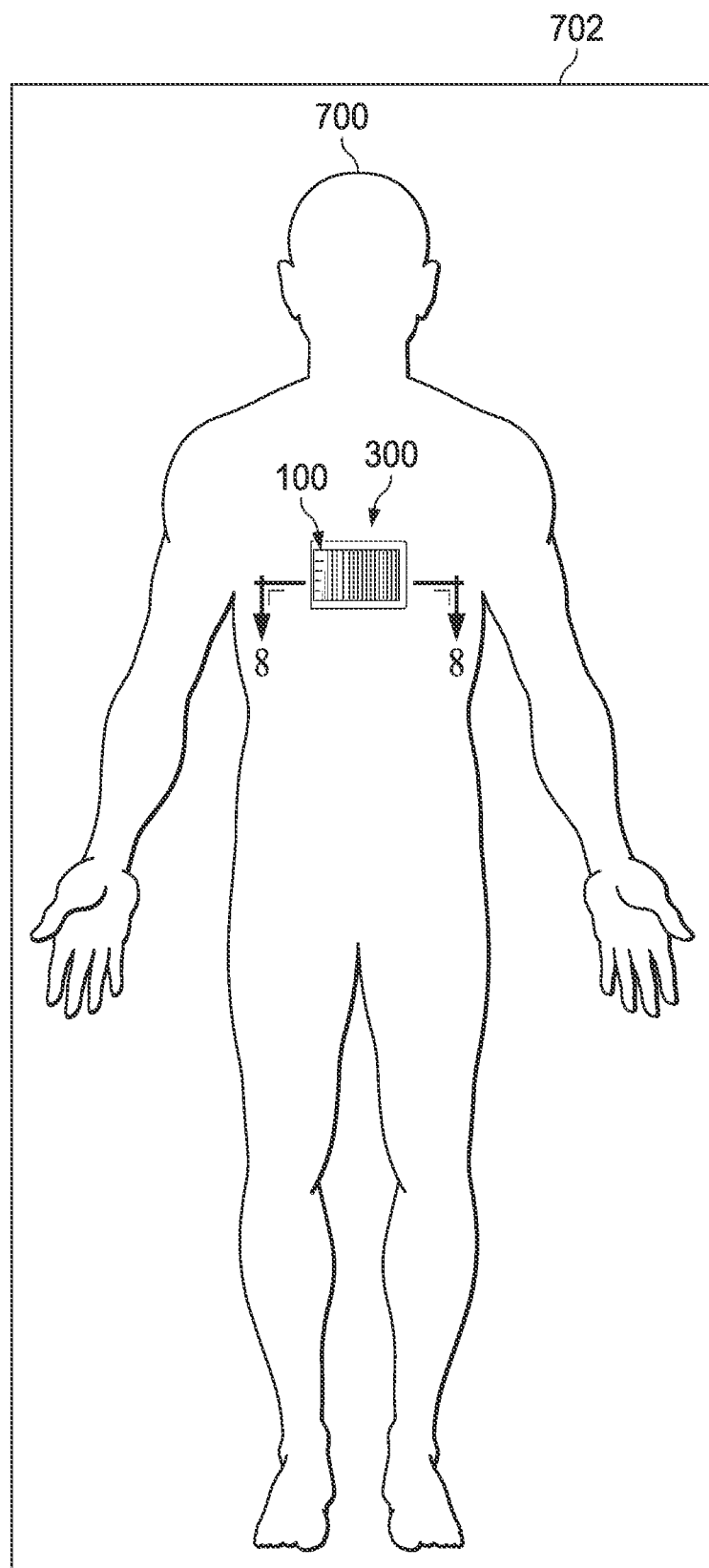
FIG. 7 is a drawing illustrating the application of marking grid with a supplemental longitudinal-positioning indicator onto a patient in accordance with an illustrative embodiment.
Figure 8:
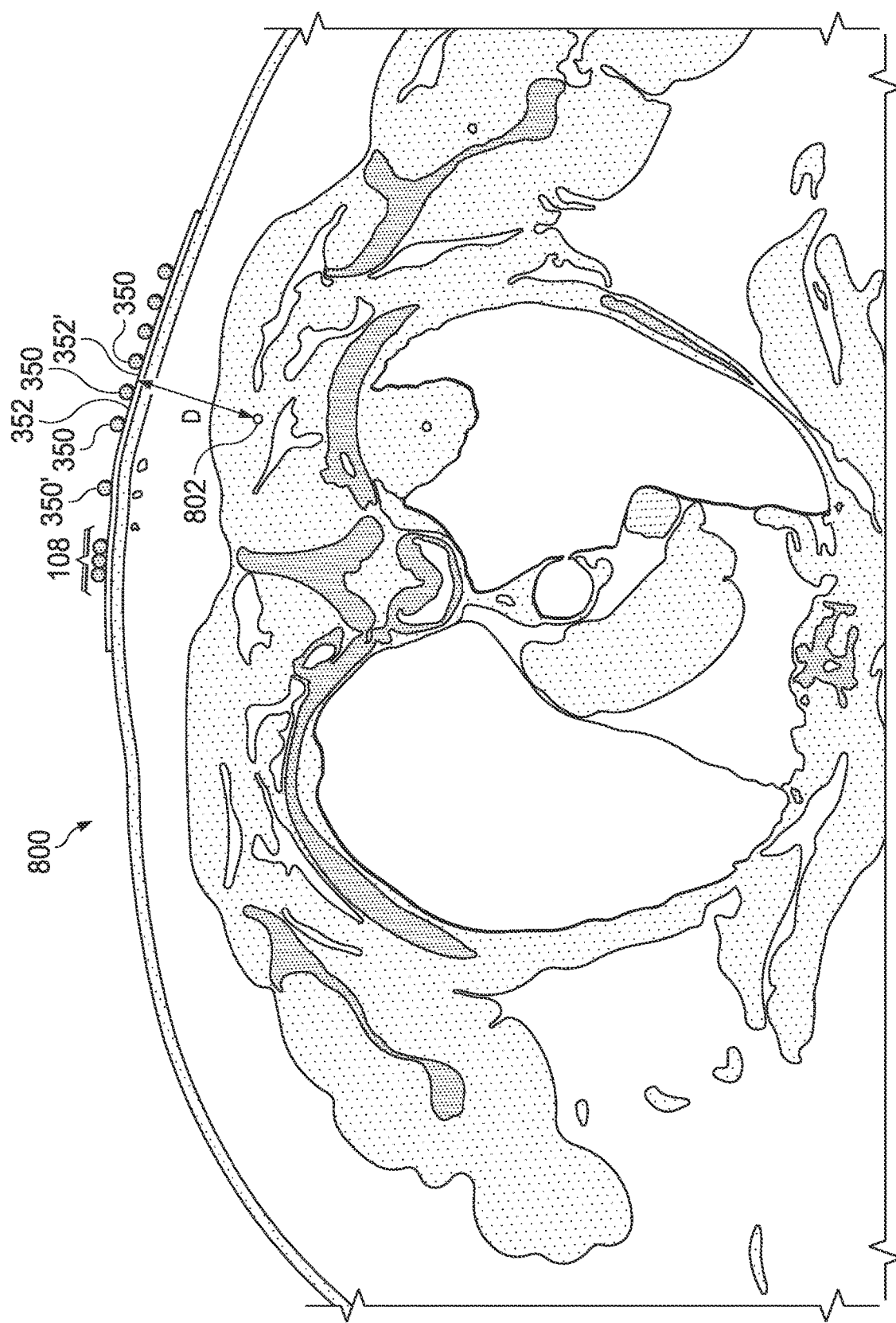
FIG. 8 is a drawing illustrating a radiographic image of a patient taken along line 8-8 in FIG. 7.

FIG. 7 is a drawing illustrating the application of a marking grid and a supplemental longitudinal-positioning indicator onto a patient in accordance with an illustrative embodiment. The marking grid 300 is applied to the skin of patient 700 and oriented so that the longitudinal-positioning guidelines are extended from head to foot, i.e., in the longitudinal direction. Further, the marking grid 300 is applied to the patient 700 so that when the patient 700 is in a supine position on the scanning table 702, the marking grid 300 and the longitudinal-positioning indicator 100 is above the targeted internal structure. Radiographic images of the patient 700 are taken in the transverse plane, an example of which is depicted in FIG. 8, taken along line 8-8 in FIG. 7. The longitudinal-positioning indicator 100 can be adhered to the marking grid 300 before or after the marking grid 300 is adhered to the skin of the patient 700 or after.

When radiographic images are taken of the patient 700, the set of lateral-positioning guidelines 350 from the marking grid 300 and the set of longitudinal-positioning guidelines 108 from the longitudinal-positioning indicator 100 provide reference markers that appear on the radiographic image 800, which can be used to identify a lateral position and a longitudinal position, respectively, on the patient's body for inserting a biopsy needle for tissue extraction. For example, a user analyzing the plurality of radiographic images taken of a patient 700 may determine that a tissue sample should be extracted from location 802. Accordingly, the user can identify a lateral-positioning coordinate from radiographic image 800 by counting the number of guidelines 350 from a reference location, e.g., the lateral-positioning guideline 350' closest to the longitudinal-positioning indicator 100, or the lateral-positioning guideline 350' separated from the others by the widest elongated aperture 352. In this illustrative embodiment, a user can count the lateral-positioning guidelines 350 to determine that the lateral-positioning coordinate should be located between the third and fourth lateral-positioning guideline 350, in the area defined by the elongated aperture 352'. The user can also determine the longitudinal-positioning coordinate based on the reference markers provided by the set of lateral-positioning guidelines 108, and a depth D for needle insertion.

Thereafter, a location for needle placement on the skin of user 700 can be identified from visual indicators on the marking grid 300 and the longitudinal-positioning indicator 100. A visual indicator for the lateral-positioning coordinate can include a numerical value printed on the marking grid 300 associated with each of the lateral-positioning guidelines 350 and a visual indicator for the longitudinal-positioning coordinate can be the index 110 that was previously described in more detail in FIG. 1.

Figure 9A:
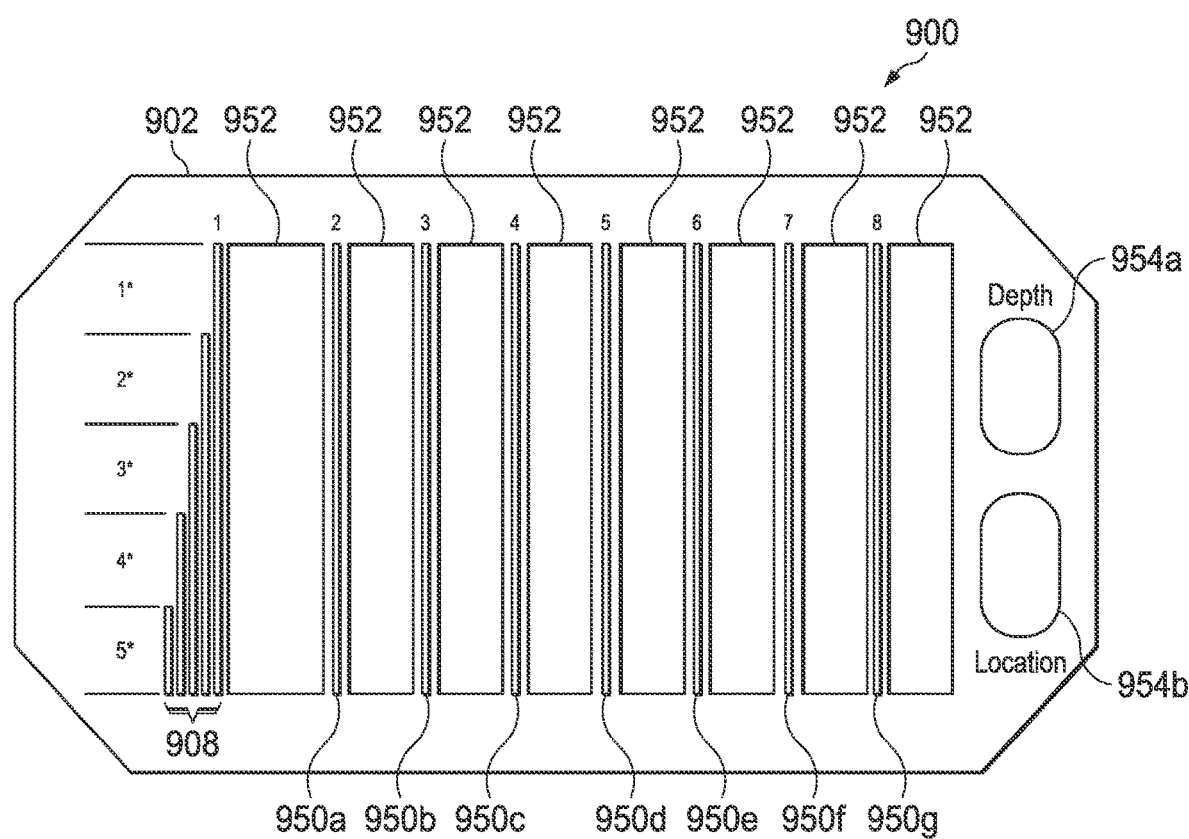
FIGS. 9A and 9B are drawings depicting a plan view and a perspective view, respectively, of a marking grid with a set of lateral-positioning guidelines and a set of longitudinal-positioning guidelines in accordance with yet another illustrative embodiment.
Figure 9B:
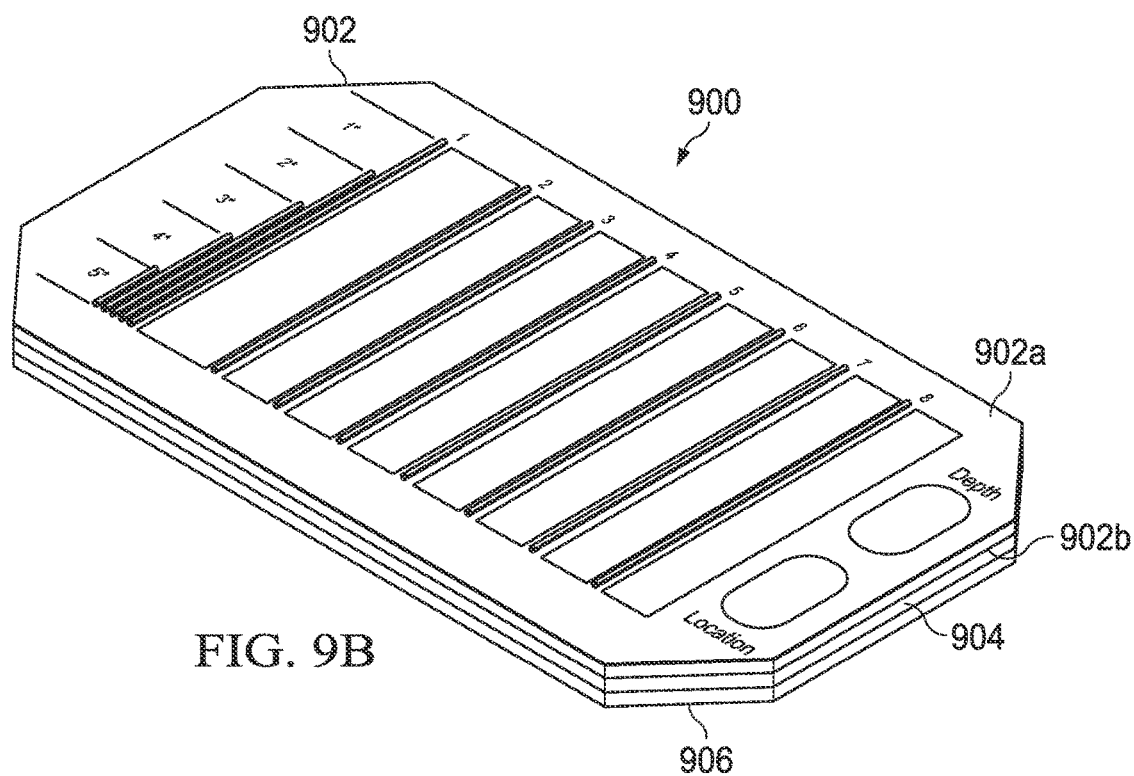

FIGS. 9A and 9B are drawings depicting a plan view and a perspective view, respectively, of a marking grid with a set of lateral-positioning guidelines and a set of longitudinal-positioning guidelines in accordance with yet another illustrative embodiment.

The marking grid 900 includes a substrate 902, which is like substrate 102 in FIG. 1. Further, the substrate has a first side 902a and a second side 902b that is at least partially coated with an adhesive 904. In a non-limiting embodiment, a releasable backing material 906 is adhered to the substrate 902 via the adhesive 904 prior to use. The substrate 902 supports the set of lateral-positioning guidelines 950 and the set of longitudinal-positioning guidelines 908. As previously described, the substrate 902 can be formed from a substantially radiolucent material, whereas the set of lateral-positioning guidelines 950 and the set of longitudinal-positioning guidelines 908 can be formed from a substantially radiopaque material to provide a sufficient contrast between the substrate 902 and the positioning guidelines 908 and 950 on a radiographic image.

In this non-limiting embodiment in FIG. 9A, the set of lateral-positioning guidelines 950 includes seven elongated guidelines 950a-950g of generally equal length, arranged in parallel fashion to divide the marking grid into a number of segments, each of which contains an elongated aperture 952. Each of the guidelines in the set of lateral-positioning guidelines 950 can be identified by a unique value, i.e., a visual indicator, for ease of identification/differentiation. In this illustrative embodiment, the unique values are arranged along the top edge. The set of lateral-positioning guidelines 950 can be used to determine a lateral-positioning coordinate in a manner that is known in the art. The set of longitudinal-positioning guidelines 908 is arranged in a stair-step fashion, as described in more detail in FIG. 1, and can be used to determine a longitudinal-positioning coordinate in a manner that was described in more detail in FIG. 2. The marking grid 900 can be applied to a patient in a manner similar to the methodology described in in FIG. 7. Further, the resultant radiographic image is similar to the radiographic image 800 in FIG. 8, and the manner in which a location can be determined, e.g., for biopsy needle placement, is determined similarly and will not be repeated for the sake of brevity.

In some embodiments, the marking grid 900 also includes notation areas 954a and 954b, which can be used to write down position information, such as depth, lateral position, and/or longitudinal position which may be conveyed to a user in close proximity to the patient.

In this illustrative embodiment in FIG. 9, the first elongated aperture 952 is wider than the remaining elongated apertures 952. Conventionally available marking grids utilized a wider elongated aperture on one side to provide context for differentiating between the left side and the right side. The marking grid 900 in FIG. 9 also includes the wider elongated aperture on one side to help users familiar with the conventional marking grids to properly align the marking grid 900. However, in another embodiment, all the elongated apertures 952 have the same width, as described in FIG. 11.

Figure 10:
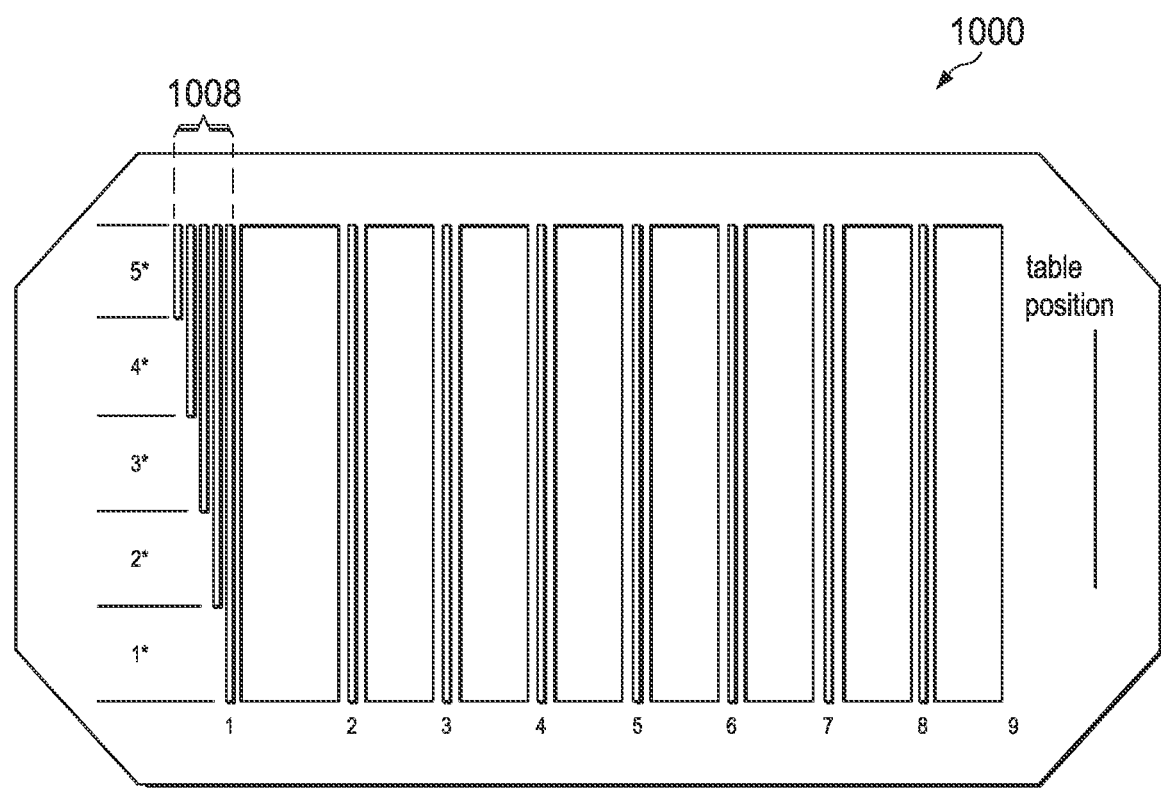
FIG. 10 is a schematic depicting a plan view of a marking grid with a set of lateral-positioning guidelines and a set of longitudinal-positioning guidelines in accordance with yet another illustrative embodiment.

FIG. 10 is a schematic depicting a plan view of a marking grid with a set of lateral-positioning guidelines and a set of longitudinal-positioning guidelines in accordance with yet another illustrative embodiment. The marking grid 1000 is similar to marking grid 900 with the exception of the set of longitudinal-positioning guidelines 1008 differs. In particular, the set of longitudinal positioning guidelines 1008 is arranged like the set of longitudinal-positioning guidelines 508 in FIG. 5.

Figure 11:
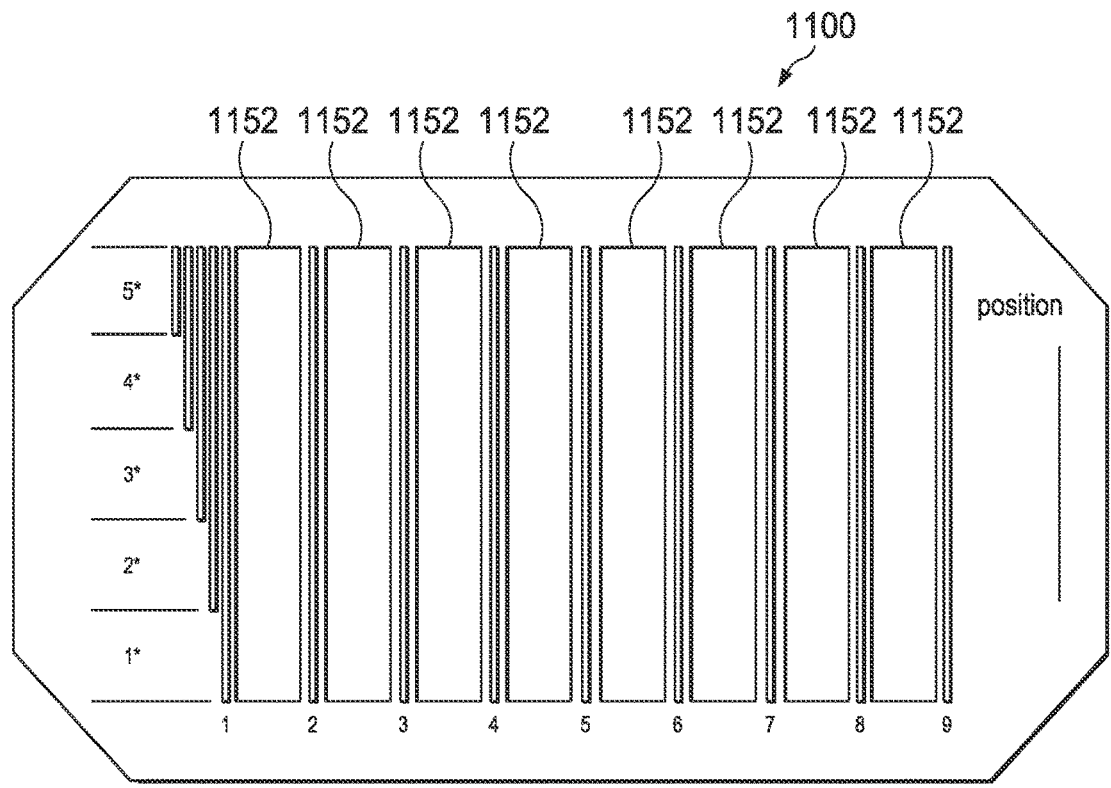
FIG. 11 is a schematic depicting a plan view of a marking grid with a set of lateral-positioning guidelines and a set of longitudinal-positioning guidelines in accordance with yet another illustrative embodiment.

FIG. 11 is a schematic depicting a plan view of a marking grid with a set of lateral-positioning guidelines and a set of longitudinal-positioning guidelines in accordance with yet another illustrative embodiment. The marking grid 1100 is similar to marking grid 1000 with the exception that each of the plurality of elongated apertures 1152 have the same width.

Figure 12:
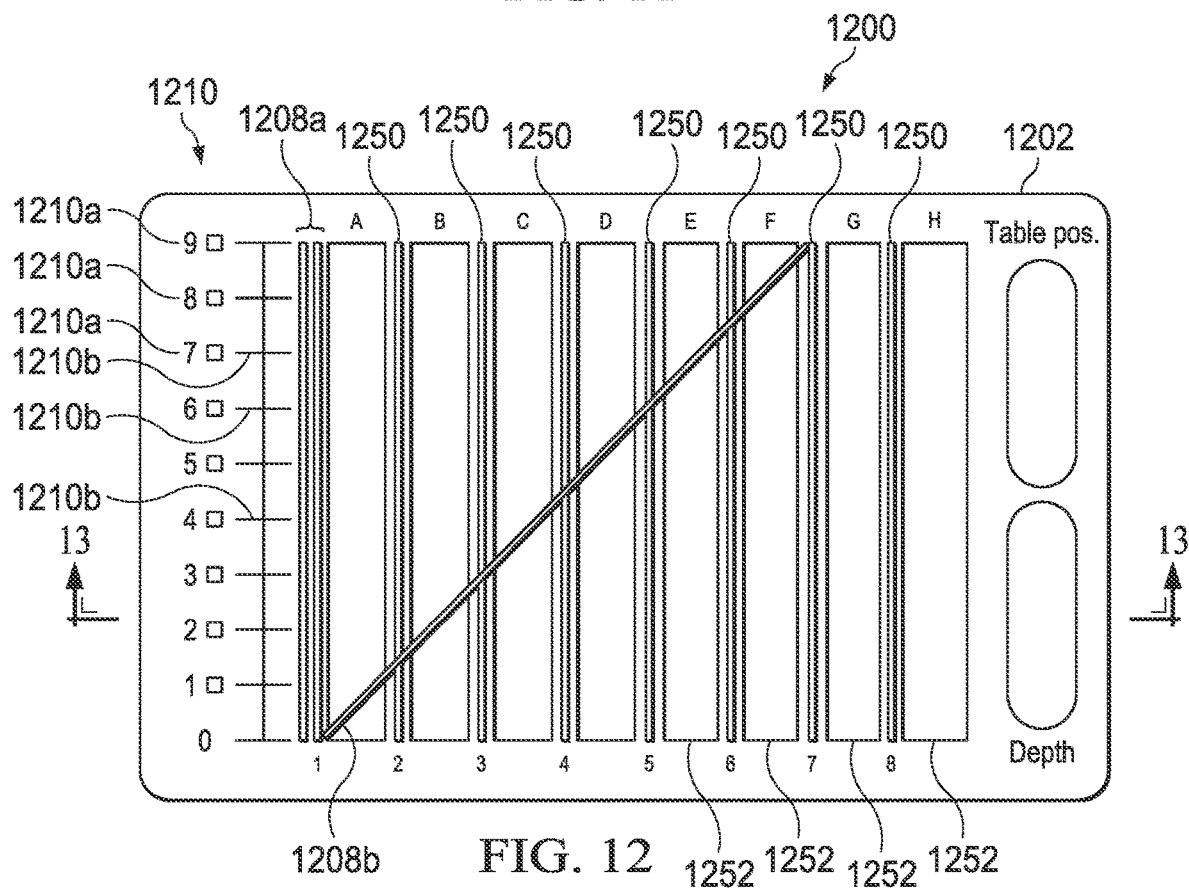
FIG. 12 is a drawing depicting a plan view of a marking grid with a set of lateral-positioning guidelines and a set of longitudinal-positioning guidelines in accordance with yet another illustrative embodiment.
Figure 13:
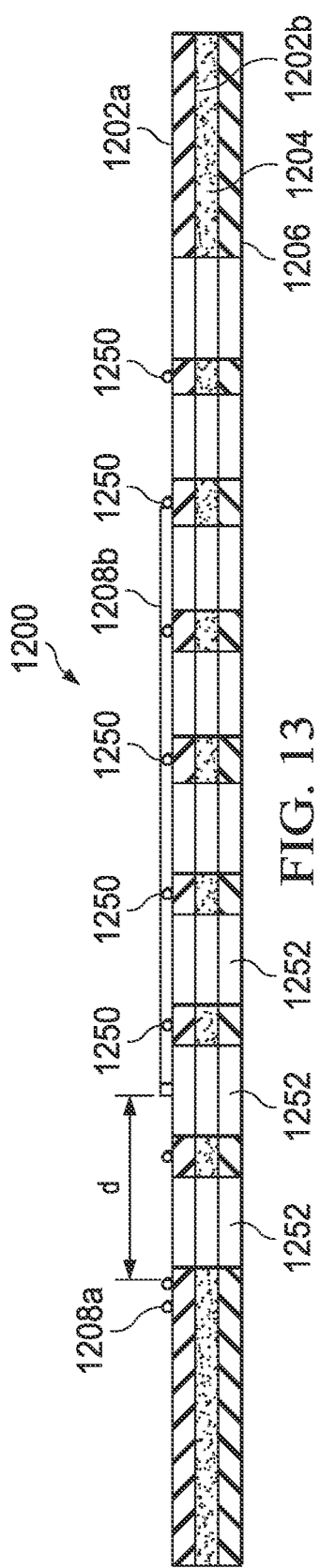
FIG. 13 is a drawing depicting a cross-sectional view of a marking grid in FIG. 12 taken along line 13-13.

FIGS. 12 and 13 are drawings depicting a plan view and a cross-sectional view, respectively, of a marking grid with a set of lateral-positioning guidelines and a set of longitudinal-positioning guidelines in accordance with yet another illustrative embodiment.

The marking grid 1200 includes a substrate 1202, which is like substrate 102 in FIG. 1. Further, the substrate 1202 has a first side 1202a and a second side 1202b that is at least partially covered by an adhesive 1204. The adhesive 1204 adheres the substrate 1202 to releasable backing material 1206 that can be removed prior to use. The substrate 1202a supports the set of lateral-positioning guidelines 1250 and the set of longitudinal-positioning guidelines 1208. As previously described in various earlier embodiments, the substrate 1202 can be formed from a substantially radiolucent material, whereas the set of lateral-positioning guidelines 1250 and the set of longitudinal-positioning guidelines 1208 can be formed from a substantially radiopaque material to provide a sufficient contrast between the substrate 1202 and the positioning guidelines 1250 and 1208 on a radiographic image.

In this non-limiting embodiment in FIGS. 12 and 13, the set of lateral-positioning guidelines 1250 includes seven elongated guidelines of generally equal length, arranged in parallel fashion to divide the marking grid into a number of segments, each of which contains an elongated aperture 1252. Each of the guidelines in the set of lateral-positioning guidelines 1250 can be identified by a unique value, i.e., a visual indicator, for ease of identification/differentiation. In this illustrative embodiment, the unique values are arranged along the bottom edge. The set of lateral-positioning guidelines 1250 can be used to determine a lateral-positioning coordinate in a manner that is known in the art.

The set of longitudinal-positioning guidelines 1208 includes a set of reference lines 1208a and an auxiliary guideline 1208b that is apart from the set of reference lines 1208a. In this illustrative embodiment in FIGS. 12 and 13, the auxiliary guideline 1208b is angled relative to the set of reference lines 1208a, and the set of reference lines 1208a includes two reference lines positioned in close proximity to each other, which allows for easy differentiation from the set of lateral-positioning guidelines 1250 in a radiographic image. In one embodiment, the phrase "close proximity" means that the two reference lines are touching, or just barely touching so that they that they appear as two distinct reference markers in a radiographic image. In another embodiment, the phrase "close proximity" also means a distance that is less than the distance between each of the set of lateral-positioning guidelines 1250.

In one embodiment, the auxiliary guideline 1208b has a distinguishing feature that allows it to be easily differentiated from the plurality of guidelines that form the set of lateral-positioning guidelines 1250. For example, the auxiliary guideline 1208b can have a larger diameter, a different shape, a different radiopacity, or different layers having different radiopacities. In the non-limiting embodiment in FIGS. 12 and 13 the auxiliary guideline 1208b has a square cross-section with a lower radiopacity than the set of lateral-positioning guidelines 150, which facilitates differentiation.

The marking grid 1200 also includes an index 1210 printed on the marking grid 1200 that can be used to determine a longitudinal-positioning coordinate on a patient once the longitudinal-positioning coordinate is identified from a radiographic image, as will be described in more detail below with reference to the cross-sectional view of marking grid 1200 shown in FIG. 13.

The cross-sectional view of marking grid 1200 in FIG. 13 is similar to the depiction of the marking grid 1200 in a radiographic image taken in a transverse plane corresponding to line 13-13 in FIG. 12. The cross-sectional view depicts each of the guidelines that form the set of lateral-positioning guidelines 1250, which can be used to determine a lateral-positioning coordinate in a manner known to those having ordinary skill in the art. A distance d between the set of reference lines 1208a and the auxiliary guideline 1208b can be determined from the radiographic image and used to determine a corresponding longitudinal-positioning coordinate, which can then be identified and/or marked on a patient's skin with reference to the various visual indicators on marking grid 1200.

In one embodiment, a known relationship between the set of reference lines 1208a and the auxiliary guideline 1208b can be used to easily determine a distance between the set of reference lies 1208a and the auxiliary guideline 1208b for easily determining a longitudinal-positioning coordinate without the need for measurement. For example, the marking grid 1200 can be configured such that the set of reference lines 1208a is considered a vertical axis in a Cartesian coordinate system (i.e., a Y-axis), and an imaginary line spanning the marking grid 1200 along the bottom and in the transverse direction, i.e., passing through the ends of each of the lateral-positioning guidelines 1250, is considered a horizontal axis in a Cartesian coordinate system (i.e., an X-axis). Further, the auxiliary line 1208b can be configured with a slope that satisfies the equation y=mx+b where the slope (x) is 1 and the y-intercept (b) is 0. Thus, with reference to FIG. 13, the distance d on the X-axis also corresponds to the same distance on the Y-axis, which is the longitudinal-positioning coordinate for determining the location on a patient's skin.

Figure 15:
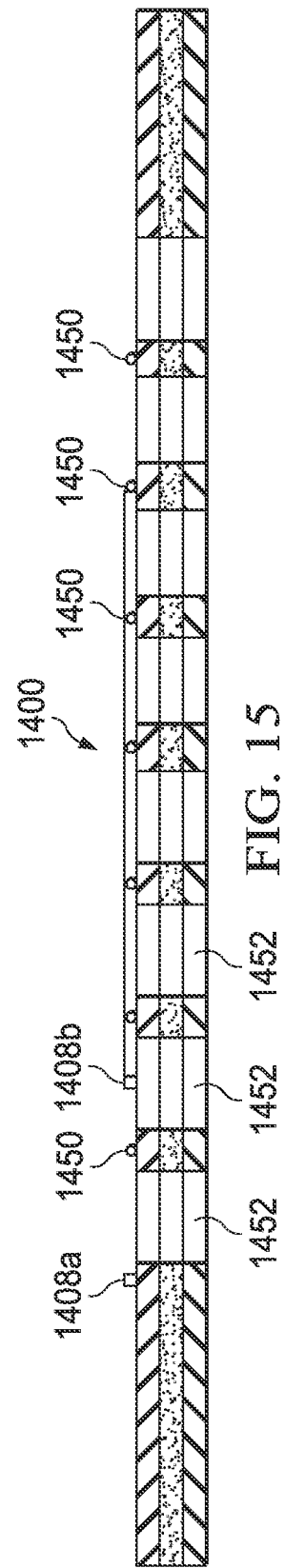
FIG. 15 is a drawing depicting a cross-sectional view of a marking grid in FIG. 14 taken along line 15-15.
Figure 14:
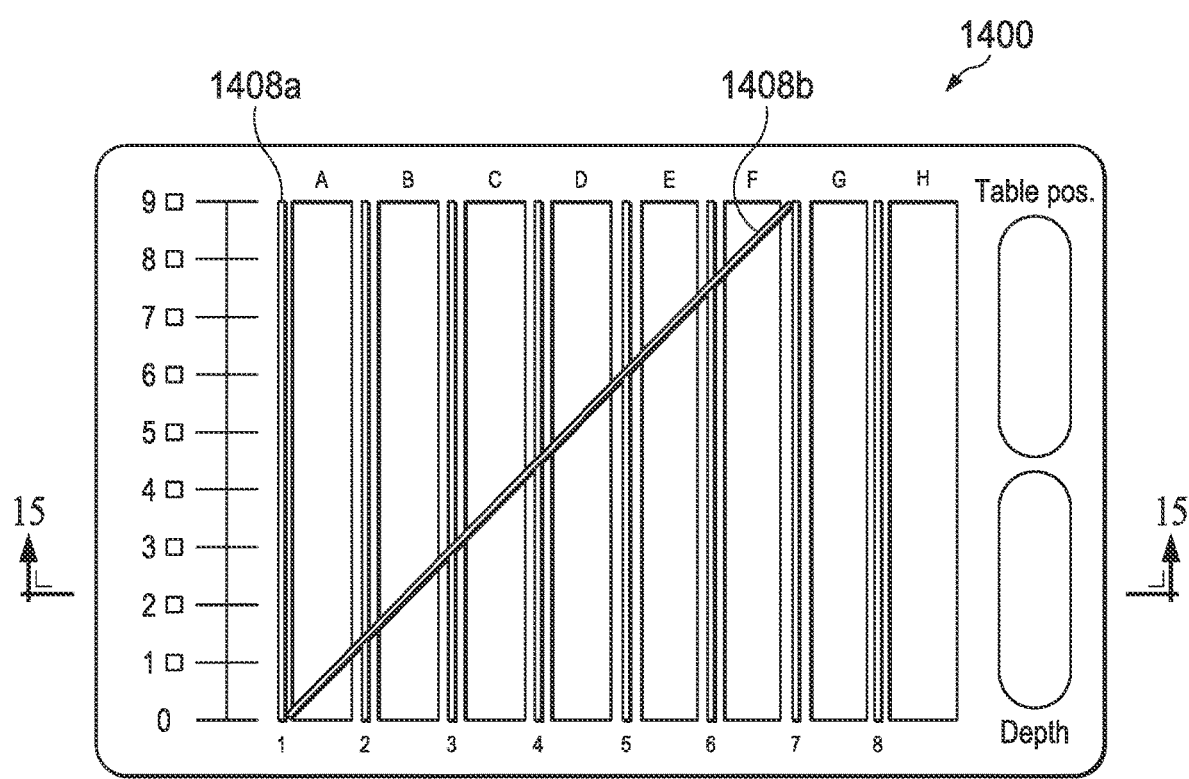
FIG. 14 is a drawing depicting a plan view of a marking grid with a set of lateral-positioning guidelines and a set of longitudinal-positioning guidelines in accordance with yet another illustrative embodiment.

FIGS. 14 and 15 are drawings depicting a plan view and a cross-sectional view, respectively, of a marking grid with a set of lateral-positioning guidelines and a set of longitudinal-positioning guidelines in accordance with yet another illustrative embodiment. The marking grid 1400 is similar to marking grid 1200 except that the set of reference lines 1408a is a single line having a square cross-section. The square cross-section of reference line 1408a can be easily differentiated from the circular cross-sections of the guidelines that form the set of lateral-positioning guidelines 1450.

In each of the embodiments depicted in FIGS. 9-15, the marking grids were depicted as having a set of elongated apertures disposed throughout the marking grid, which allows for marking a patient's skin and conducting the biopsy needle insertion without removing the marking grid. However, in another embodiment, the elongated apertures may be omitted entirely and replaced with a semipermeable material, such as a paper or fabric, that permits transfer of ink through to a patient's skin and which permits biopsy needle insertion without removing the marking grid. In this alternate embodiment, the substrate may be partially or entirely formed from the semipermeable material.

Figure 16:
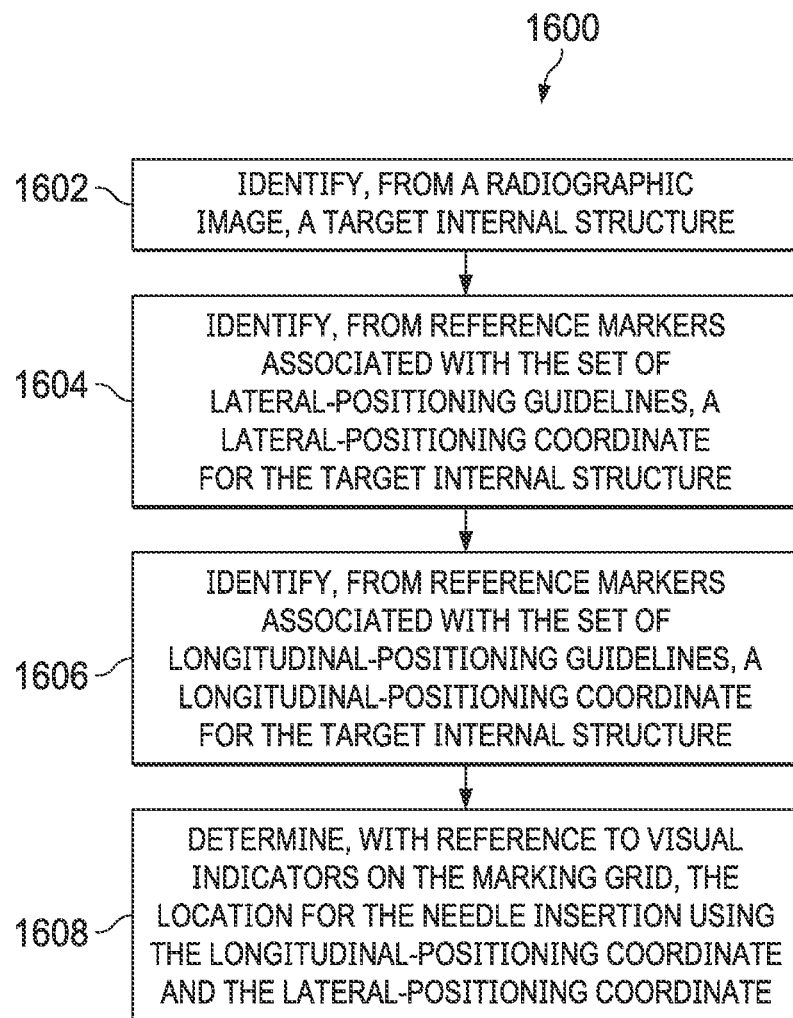
FIG. 16 is a flowchart of a process for location identification using a marking grid in accordance with an illustrative embodiment.

FIG. 16 illustrates a flowchart of a process for location identification using a marking grid in accordance with an illustrative embodiment. Flowchart 1600 begins at Step 1602 by identifying, from a radiographic image, a target internal structure. In Step 1604, a lateral-positioning coordinate is identified from reference markers associated with the set of lateral-positioning guidelines.

In Step 1606, a longitudinal-positioning coordinate is identified from reference markers associated with the set of longitudinal-positioning guidelines. In one embodiment, the set of longitudinal-positioning guidelines includes a plurality of guidelines configured to indicate a longitudinal position within the area bounded by the marking grid based on a number of guidelines that appear in the cross-section of the marking grid. In another embodiment, the set of longitudinal-positioning guidelines includes a set of reference guidelines and an auxiliary guideline, the longitudinal-positioning coordinate determined based on a distance between the set of reference guidelines and the auxiliary guideline.

In Step 1608, a location for needle insertion is determined with positional information derived from the radiographic image. In some embodiments, an optional depth measurement can be determined from the radiographic image and used for biopsy needle insertion for tissue extraction.

ADDITIONAL EMBODIMENTS

The following descriptive embodiments are offered in further support of the disclosed invention:

In a first embodiment, novel aspects of the present disclosure are directed to a longitudinal-positioning indicator that comprises a substrate including a first side and a second side, wherein the second side is at least partially coated with an adhesive; and a set of longitudinal-positioning guidelines secured with the substrate, wherein the set of longitudinal-positioning guidelines is configured to indicate a position along a length of the longitudinal-positioning guidelines based on a cross-section of the longitudinal-positioning indicator taken substantially orthogonally to the set of longitudinal-positioning guidelines.

In another aspect of the first embodiment, the longitudinal-positioning indicator comprises a substrate including a first side and a second side, wherein the second side is at least partially coated with an adhesive; a set of longitudinal-positioning guidelines secured with the substrate, wherein the set of longitudinal-positioning guidelines is configured to indicate a position along a length of the longitudinal-positioning guidelines based on a cross-section of the longitudinal-positioning indicator taken substantially orthogonally to the set of longitudinal-positioning guidelines; and further comprises one or more limitations selected from the following:
- wherein the set of longitudinal-positioning guidelines is disposed on the first side of the substrate;
- wherein the substrate has a first radiopacity, and the set of longitudinal-positioning guidelines has a second radiopacity that is greater than the first radiopacity;
- wherein the set of longitudinal-positioning guidelines is formed from a plurality of guidelines of different lengths;
- wherein the plurality of guidelines of different lengths are spaced apart and oriented substantially parallel to each other, and each of the plurality of guidelines is aligned at one end and arranged based on length;
- wherein the longitudinal-positioning indicator further comprises an index with a plurality of demarcations, each of the plurality of demarcations corresponding to a length of a guideline in the plurality of guidelines;
- wherein the substrate of the longitudinal-positioning indicator further comprises an elongated body portion for the set of longitudinal-positioning guidelines and a margin portion extending from the elongated body portion;

wherein the margin portion includes a set of tabs; and wherein the longitudinal-positioning indicator further comprises a releasable backing secured to the substrate by the adhesive.

In a second embodiment, novel aspects of the present disclosure are directed to a marking grid that comprises a substrate including a first side and a second side, wherein the second side is at least partially coated with an adhesive; a set of longitudinal-positioning guidelines supported by the substrate, and wherein the set of lateral-positioning guidelines and the set of longitudinal-positioning guidelines are configured to provide a pair of orthogonal coordinates that indicate a location within an area bounded by the marking grid, the location based on a cross-section of the marking grid taken substantially orthogonally to the set lateral-positioning guidelines.

In another aspect of the second embodiment, novel aspects of the present disclosure are directed to a marking grid that comprises a substrate including a first side and a second side, wherein the second side is at least partially coated with an adhesive; a set of longitudinal-positioning guidelines supported by the substrate, wherein the set of lateral-positioning guidelines and the set of longitudinal-positioning guidelines are configured to provide a pair of orthogonal coordinates that indicate a location within an area bounded by the marking grid, the location based on a cross-section of the marking grid taken substantially orthogonally to the set lateral-positioning guidelines; and further comprises one or more limitations selected from the following:

wherein the substrate comprises a set of elongated apertures interspersed with the set of lateral-positioning guidelines in alternating fashion;

wherein the set of longitudinal-positioning guidelines includes a plurality of guidelines, and wherein the set of longitudinal-positioning guidelines is configured to indicate a longitudinal position within the area bounded by the marking grid based on a number of guidelines that appear in the cross-section of the marking grid;

wherein the plurality of guidelines includes guidelines of a different length, arranged in a stair-step configuration;

wherein the marking grid further comprises an index with a plurality of demarcations, each of the plurality of demarcations corresponding to a length of a guideline in the plurality of guidelines;

wherein the set of longitudinal-positioning guidelines includes a set of reference guidelines and an auxiliary guideline, and wherein a longitudinal-positioning coordinate is determined based on a distance between the set of reference guidelines and the auxiliary guideline;

wherein the set of reference guidelines includes two parallel lines, and wherein the auxiliary guideline has a cross-section that differs from cross-sections of the two parallel lines; and wherein the set of reference guidelines includes one line, and where the set of reference guidelines and the auxiliary guideline have rectangular cross-sections.

In a third embodiment, novel aspects of the present disclosure are directed to a method for identifying a location for needle insertion into a patient within an area defined by a marking grid, the marking grid including a set of lateral-positioning guidelines and a set of longitudinal-positioning guidelines configured to provide reference markers based on a cross-section of the marking grid taken substantially orthogonally to the set of lateral-positioning guidelines, the method comprising: identifying, from a radiographic image, a target internal structure; identifying, from reference markers associated with the set of lateral-positioning guidelines, a lateral-positioning coordinate for the target internal structure; identifying, from reference markers associated with the set of longitudinal-positioning guidelines, a longitudinal-positioning coordinate for the target internal structure; and determining, with reference to visual indicators on the marking grid, a location for the needle insertion using the longitudinal-positioning coordinate and the lateral-positioning coordinate.

In another aspect of the third embodiment, novel aspects of the present disclosure are directed to a method for identifying a location for needle insertion into a patient within an area defined by a marking grid, the marking grid including a set of lateral-positioning guidelines and a set of longitudinal-positioning guidelines configured to provide reference markers based on a cross-section of the marking grid taken substantially orthogonally to the set of lateral-positioning guidelines, the method comprising: identifying, from a radiographic image, a target internal structure; identifying, from reference markers associated with the set of lateral-positioning guidelines, a lateral-positioning coordinate for the target internal structure; identifying, from reference markers associated with the set of longitudinal-positioning guidelines, a longitudinal-positioning coordinate for the target internal structure; determining, with reference to visual indicators on the marking grid, a location for the needle insertion using the longitudinal-positioning coordinate and the lateral-positioning coordinate; and further comprises one or more limitations selected from the following:

wherein the set of longitudinal-positioning guidelines includes a plurality of guidelines, and wherein the set of longitudinal-positioning guidelines is configured to indicate a longitudinal position within the area bounded by the marking grid based on a number of guidelines that appear in the cross-section of the marking grid; and wherein the set of longitudinal-positioning guidelines includes a set of reference guidelines and an auxiliary guideline, and wherein a longitudinal-positioning coordinate is determined based on a distance between the set of reference guidelines and the auxiliary guideline.

Although embodiments of the invention have been described with reference to several elements, any element described in the embodiments described herein are exemplary and can be omitted, substituted, added, combined, or rearranged as applicable to form new embodiments. A skilled person, upon reading the present specification, would recognize that such additional embodiments are effectively disclosed herein. Additionally, where an embodiment is described herein as comprising some element or group of elements, additional embodiments can consist essentially of or consist of the element or group of elements. Also, although the open-ended term "comprises" is generally used herein, additional embodiments can be formed by substituting the terms "consisting essentially of" or "consisting of."

While this disclosure has been particularly shown and described with reference to preferred embodiments, it will be understood by those skilled in the art that various changes in form and detail may be made therein without departing from the spirit and scope of the invention. The inventors expect skilled artisans to employ such variations as appropriate, and the inventors intend the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. A longitudinal-positioning indicator comprising:
   a substrate including a first side and a second side, wherein the second side is at least partially coated with an adhesive, and wherein the substrate has a length and a width; and
   a set of longitudinal-positioning guidelines secured with the substrate, wherein the set of longitudinal-positioning guidelines is configured to indicate a position along the length of the substrate based on a cross-section of the longitudinal-positioning indicator taken along the width of the substrate.

2. The longitudinal-positioning indicator of claim 1, wherein the set of longitudinal-positioning guidelines includes a plurality of parallel guidelines of different lengths, and wherein each of the plurality of parallel guidelines extends in a direction parallel to the length.

3. The longitudinal-positioning indicator of claim 2, wherein:
   the plurality of guidelines of different lengths are spaced apart and oriented substantially parallel to each other; and
   each of the plurality of guidelines is aligned at one end and arranged based on length.

4. The longitudinal-positioning indicator of claim 3, further comprising:
   an index with a plurality of demarcations, each of the plurality of demarcations corresponding to a length of a guideline in the plurality of guidelines.

5. The longitudinal-positioning indicator of claim 2, wherein the position along the length of the substrate is indicated by a number of the plurality of parallel guidelines appear in the cross-section of the substrate.

6. The longitudinal-positioning indicator of claim 1, wherein the set of longitudinal-positioning guidelines is disposed on the first side of the substrate.

7. The longitudinal-positioning indicator of claim 1, wherein:
   the substrate has a first radiopacity; and
   the set of longitudinal-positioning guidelines has a second radiopacity that is greater than the first radiopacity.

8. The longitudinal-positioning indicator of claim 1, wherein the substrate further comprises:
   an elongated body portion for the set of longitudinal-positioning guidelines; and
   a margin portion extending from the elongated body portion.

9. The longitudinal-positioning indicator of claim/ wherein the margin portion includes a set of tabs.

10. The longitudinal-positioning indicator of claim 8, wherein the elongated body portion is separated from the margin portion by a perforation line.

11. The longitudinal-positioning indicator of claim 1, further comprising:
    a releasable backing secured to the substrate by the adhesive.

12. A marking grid for use in radiographic imaging, the marking grid comprising:
    a substrate including a first side and a second side, wherein the second side is at least partially coated with an adhesive, and wherein the substrate includes a length and a width;
    a set of lateral-positioning guidelines supported by the substrate and extending in a direction of the length; and
    a set of longitudinal-positioning guidelines supported by the substrate, and
    wherein the set of lateral-positioning guidelines and the set of longitudinal-positioning guidelines are configured to identify a location within an area bounded by the marking grid, the location based on a cross-section of the marking grid taken substantially orthogonally to the length of the substrate.

13. The longitudinal-positioning indicator of claim 12, wherein the set of longitudinal-positioning guidelines includes at least one reference guideline extending in a direction parallel to the length and an auxiliary guideline at a predetermined angle relative to the at least one reference guideline.

14. The longitudinal-positioning indicator of claim 13, wherein the auxiliary guideline intersects at least some of the set of lateral positioning guidelines.

15. The marking grid of claim 12, wherein the substrate comprises a set of elongated apertures interspersed with the set of lateral-positioning guidelines in alternating fashion.

16. The marking grid of claim 12, wherein the set of longitudinal-positioning guidelines includes a plurality of guidelines, and wherein the set of longitudinal-positioning guidelines is configured to indicate a longitudinal position within the area bounded by the marking grid based on a number of guidelines that appear in the cross-section of the marking grid.

17. The marking grid of claim 16, wherein the plurality of guidelines includes guidelines of a different length, arranged in a stair-step configuration.

18. The marking grid of claim 16, wherein the marking grid further comprises:
    an index with a plurality of demarcations, each of the plurality of demarcations corresponding to a length of a guideline in the plurality of guidelines.

19. The marking grid of claim 12, further comprising a releasable backing secured to the substrate by the adhesive.

* * * * *